United States Patent
Gould et al.

(10) Patent No.: US 8,287,809 B2
(45) Date of Patent: *Oct. 16, 2012

(54) METHOD FOR STIMULATING SALIVA PRODUCTION DURING ORAL SAMPLE COLLECTION PROCEDURE

(75) Inventors: Martin Gould, Mullica Hill, NJ (US); Robert Smalley, Mantua, NJ (US); Robert Bernstine, Chesapeake City, MD (US)

(73) Assignee: American Bio Medica Corporation, Kinderhook, NY (US)

( * ) Notice: Subject to any disclaimer, the term of this patent is extended or adjusted under 35 U.S.C. 154(b) by 1436 days.

This patent is subject to a terminal disclaimer.

(21) Appl. No.: 11/760,977

(22) Filed: Jun. 11, 2007

(65) Prior Publication Data

US 2008/0305548 A1     Dec. 11, 2008

(51) Int. Cl.
    *G01N 15/06* (2006.01)
(52) U.S. Cl. ..................................................... 422/68.1
(58) Field of Classification Search .................. None
    See application file for complete search history.

(56) References Cited

U.S. PATENT DOCUMENTS

| | | | |
|---|---|---|---|
| 5,211,182 A | 5/1993 | Deutsch et al. | |
| 5,630,986 A | 5/1997 | Charlton et al. | |
| 5,830,154 A | 11/1998 | Goldstein et al. | |
| 6,214,629 B1 | 4/2001 | Freitag et al. | |
| 6,267,722 B1 | 7/2001 | Anderson et al. | |
| 6,440,087 B1 | 8/2002 | Sangha | |
| 6,464,939 B1 | 10/2002 | Bachand et al. | |
| 6,468,474 B2 | 10/2002 | Bachand et al. | |
| 6,489,172 B1 | 12/2002 | Bachand et al. | |
| 6,524,530 B1 | 2/2003 | Igarashi et al. | |
| 6,634,243 B1 | 10/2003 | Wickstead et al. | |
| 6,926,678 B1 | 8/2005 | Cesarczyk | |
| 7,695,953 B2 * | 4/2010 | Gould et al. | 435/287.2 |
| 7,700,305 B2 * | 4/2010 | Toranto et al. | 435/7.21 |
| 2001/0008614 A1 * | 7/2001 | Aronowitz | 422/101 |
| 2001/0012637 A1 | 8/2001 | Casterlin et al. | |
| 2004/0184954 A1 * | 9/2004 | Guo et al. | 422/56 |
| 2007/0062460 A1 * | 3/2007 | Simer | 119/709 |

FOREIGN PATENT DOCUMENTS

EP            520408            12/1992

* cited by examiner

*Primary Examiner* — Ann Lam
(74) *Attorney, Agent, or Firm* — B. Aaron Schulman, Esq.; Stites & Harbison PLLC (57) ABSTRACT

A method and device are provided for stimulating and increasing the production of saliva during immunoassay tests for drugs or other analytes wherein a scent or odor capable of stimulating saliva production is incorporated into a device for obtaining an oral sample from a test subject. The scent or odor may be impregnated into the oral sample collection device or may be part of an attachment to such a device, and the scent or odor is disposed in such a manner so as to maximize the exposure of the scent to the test subject and thus stimulate the production of saliva. The method and device of the invention are advantageous because the increased production of saliva will facilitate the testing of an oral sample for drugs or other analytes and will increase the likelihood of obtaining a complete and accurate result.

21 Claims, 8 Drawing Sheets

METHOD FOR STIMULATING SALIVA PRODUCTION DURING ORAL SAMPLE COLLECTION PROCEDURE

FIELD OF THE INVENTION

The present invention relates generally to diagnostic tests involving collection of an oral sample such as saliva for tests of an analyte such as a drug of abuse, and more particularly to a method of stimulating saliva production so as to greatly increase the amount of saliva that can be accumulated in such a procedure and thus substantially improve the accuracy and sensitivity of such testing.

BACKGROUND OF THE INVENTION

The increased availability and use of drugs of abuse along with the need for testing of other analytes, for example HIV or antibodies thereto, has caused employers, governmental agencies, sports groups, hospital emergency rooms and other organizations to utilize drug and analyte screening methods in a wide variety of situations such as in screening individuals for potential employment or purchasing insurance, or in order to maintain safety in the work place. In addition, in law enforcement, there is a constant need for providing improved on-the-spot testing for drugs of abuse or other analytes in a quick and simple manner since these tests will be far removed from the clinical setting. Screening tests for the detection of drugs of abuse and other analytes range in complexity from simple immunoassay tests to very complex analytical procedures.

Over the years the speed and specificity of immunoassays have made them one of the most accepted methods for screening for drugs of abuse in body fluids. Typical drug screening tests are performed for the purpose of quickly identifying on a qualitative basis, the presence of drugs in a body fluid which may be urine or saliva. A complete analysis of the sample may then be carried out in a laboratory only if the preliminary screening results are positive. More and more such drug screenings are taking place on site or at the work place, or during routine police stops or check points, and these are generally carried out by testing personnel who are generally not technically trained as would be a laboratory technician. It is thus important that the drug screening procedure is simple but yet reliable. Further, the test apparatus must be designed so as to enable the testing personnel to avoid all contact with the fluid specimen which is being tested.

While blood and urine samples have long been the primary fluids used for testing for disease as well as for evidence of substance abuse, there is increasing interest in testing regimens which can test a variety of oral samples including salivary specimens. Some advantages in a system that can test saliva include that it is relatively easy to obtain a saliva sample and that a saliva sample obtained on the spot cannot be adulterated. Also, saliva testing is more suitable in testing of recent use since it does not maintain reactivity of the analyte after use for up to four to six weeks. Accordingly, testing of saliva gives a result in real time within a span of hours as compared to urine which gives a test result after-the-fact. In general, saliva is useful to measure impairment as opposed to other tests, e.g., urine tests, which are generally not suitable for this purpose.

However, the ability to collect and analyze oral samples such as saliva for diagnostic purposes is complicated by the relatively high viscosity of the fluid and the small volumes of salivary fluid secreted. In particular, saliva contains mucins which are a family of large, heavily glycosylated proteins which account for many of the properties of saliva. These mucins also act to disrupt or inhibit the lateral flow necessary to achieve a rapid and accurate test result and greatly restrict both the time it takes for a sample to travel through the immunoassay strip as well as the amount of the target compound in the sample which can travel up the strip and thus be determined by the immunoassay.

Because of the problems caused by mucins, certain testing systems had recommended long and elaborate procedures for removing mucins prior to testing the sample. These procedures include pre-treating a sample such as saliva with a diluent or other reagent which is capable of breaking down the interferants in a sample, e.g., mucins in saliva, so that these interferants do not restrict the capillary flow of the sample through the test strip, in order to try to achieve a rapid test of target compounds. However, these pre-treatment steps with specific reagents to dilute or denature interferants, modify analyte structure, or release analyte from binders, must generally be performed outside the confines of the test device, and this incurs additional steps and solutions which must be handled by the persons administering the test. For example, it is necessary to suitably collect the sample, have the sample expressed into a buffer solution, and then dispensed into a reaction well which generally contains a second reagent such as an identifying reagent, which can be bound to a materials that can bind to the target antigen, all before the testing solution including the sample is introduced onto an immunoassay test strip. All these steps necessitate the development of means and techniques for constructing self-contained devices which can test for saliva in a manner that allows one to safely and efficiently control the test sample during pre-treatment and testing, but is still safe and simple to use and also able to obtain accurate results.

Previously, others have attempted to develop devices to test saliva, but none have provided a safe, quick and effective means for testing a variety of body fluids including saliva which can be used in a variety of settings including on-the-spot testing in addition to testing in the workplace setting by non-professional testing personnel. For example, U.S. Pat. No. 6,634,243 issued to Wickstead relates to a device which has an inadequate and ineffective provision for control of the test sample. Other art in this field includes U.S. Pat. No. 6,267,722 issued to Anderson et al, U.S. Pat. No. 6,214,629 issued to Freitag et al., and U.S. Pat. No. 5,630,986 issued to Charlton et al. In addition, U.S. Pat. Nos. 6,464,939, 6,468, 474 and 6,489,172, each issued to Bachand et al, disclose other saliva testing devices which also do not allow for quick and efficient break down of mucins so as to facilitate a highly sensitive test for a drug of abuse from a saliva sample. Finally, other devices are shown in U.S. Pat. No. 6,524,530 and in European Patent Application 520,408 A1, but once again these references do not disclose a flexible testing system which can suitably handle the problems associated with saliva testing, in particular the presence of interferants such as mucins which can reduce lateral flow and greatly impair the accuracy and usefulness of the tests.

More recently, an improved system to collect saliva and other bodily fluids was disclosed in U.S. patent application Ser. No. 11/621,261, said application incorporated herein by reference, which included a self-contained device that could test for saliva and which promoted the breakdown of mucins. However, the sensitivity of such a system when used in a saliva test may still be limited in cases where the test subject cannot produce sufficient saliva for the test, a condition otherwise known as "dry mouth", i.e., little or no saliva flow, and this will generally result in no result or an unreliable result.

It thus remains a highly desirable object to develop methods for conducting tests of analytes in oral samples quickly and accurately, and in which saliva production in a test subject undergoing saliva testing can be increased rapidly, as would be necessary at a drug test that might be taken by a law enforcement officer after a traffic stop, or other similar "point-of-use" testing for drugs or other analytes.

SUMMARY OF THE INVENTION

It is thus an object of the present invention to provide a safe and effective method for rapidly increasing the saliva production of a test subject who may be subject to a test of an oral sample such as saliva so that the test can be carried out quickly and accurately with sufficient amount of collected sample to complete the test.

It is another object of the present invention to provide a testing system and apparatus for analytes in an oral sample such as saliva that can stimulate saliva production at the same time a saliva test is being administered so as to increase saliva output, increase the volume of saliva collected by the device, and to greatly increase the likelihood that the test results will be accurate.

It is a further object of the present invention to provide a device and method for carrying out simple but accurate tests of a sample obtained from a swab of a subject's mouth which will be useful in "point-of-use" testing which will allow the test to be conducted quicker and more accurately that heretofore possible.

It is still further an object of the present invention to provide a device and method for carrying out oral sample testing on individuals who have "dry mouth" and on whom such testing would be otherwise inaccurate or impossible to conduct.

The objects of the present invention are achieved and the disadvantages of the prior art are eliminated by the method and device according to the present invention whereby a scent or odor capable of stimulating saliva production is incorporated in a suitable device for obtaining an oral sample from a test subject and using that sample in an immunoassay in order to determine the presence of the level of an analyte such as a drug of abuse in the sample. This may be done in a variety of ways, such as the application of a scent-containing adhesive to a wand used in obtaining the oral sample, the impregnation of a scent or odor into the plastic material used in a device to collect saliva or other oral sample, or even the provision of a separate plastic piece to the device used to collect an oral sample, such as a scented clip which may be attached to the collection device. In the preferred embodiment, the scented portion is positioned on the collection device so as to be maintained outside of the mouth while the sample is collected, and it is generally preferred that the scented portion be brought into proximity with the test-subject's nostrils or nasal passage during the collection of an oral sample. In this manner, the collecting device may be used more effectively in obtaining an oral sample when desired, e.g., for testing of drugs or other analytes.

Other features and advantages of the present invention will be described in, or will be obvious from, the detailed description provided hereinbelow.

BRIEF DESCRIPTION OF THE DRAWINGS

Other objects and advantages of the present invention will be apparent upon reference to the accompanying descriptions when taken in conjunction with the following drawings, which are exemplary, wherein:

FIG. 8b is a side, partially cut-away view of the alternate embodiment as depicted in FIG. 8a.

DETAILED DESCRIPTION OF THE INVENTION

Proceeding next to the drawings wherein like reference symbols indicate the same parts throughout the various views, the present invention including exemplary embodiments and modifications thereof, will be described in detail.

In accordance with the present invention, the objects of the present invention are achieved and the disadvantages of the prior art are eliminated by the method and device according to the present invention whereby a scent or odor capable of stimulating saliva production is incorporated in a suitable collection device for obtaining a saliva sample from a test subject and using that saliva sample in an immunoassay in order to determine the presence of the level of an analyte such as a drug of abuse in the sample. As will be described further below, this may be done in a variety of ways, such as the application of a scent-containing adhesive to a wand used in obtaining the oral sample, the impregnation of a scent or odor into the plastic material used in a device to collect saliva or other oral sample, or the provision of a separate plastic piece to the device used to collect an oral sample, such as a scented clip which may be attached to the collection device. In the preferred embodiment, the scented portion is positioned on the collection device so as to be maintained outside of the mouth while the sample is collected, and it is generally preferred that the scented portion be brought into proximity with the test-subject's nasal passage during the collection of an oral sample. In this manner, the collecting device may be used more effectively in obtaining an oral sample when desired, e.g., for testing of drugs or other analytes.

One such suitable collecting device is disclosed in U.S. patent application Ser. No. 11/621,261, said application incorporated herein by reference, and this application refers to a device wherein a collecting wand having an absorbent material such as a sponge or other suitable absorbent material at its distal end, and in one embodiment the device can be inserted into the mouth of the patient in order to obtain an oral sample, e.g., of saliva, buccal cavity fluid, buccal cells, etc. In the general process of obtaining and expressing the desired oral sample, a suitable collection wand with absorbent material is inserted into the mouth of the test subject to collect a sample, and once the sample is collected, the absorbent containing the sample is expressed into a suitable means for conducting an analysis of desired drugs or other analytes in the sample. In one such process, such as described in U.S. patent application Ser. No. 11/621,261, the sample in the absorbent material is first expressed into a vial containing a buffer so as to increase the expression of the oral sample from the absorbent material and increase the efficiency of the testing procedure, and the sample is expressed from the absorbent by means of a thick portion of the wand which may be used to compress the absorbent and expel the collected sample. However, there are many other applications wherein the increase in the volume of an oral sample that will be absorbed in the sponge or other absorbent material of a collector wand is desired, and thus the invention contemplates use in any system wherein an oral sample may be subject to drug/analyte testing procedures which utilize an oral sample collected by means of a suitable absorbent. Accordingly, although one may utilize the present device in a system which involves a step of buffering the oral sample after collection, the device may also be used in any system wherein a drug or analyte test is conducted wherein the sample is taken from the mouth of a patient using a wand and an absorbent at one end of the wand, and then subject to a test for analytes in the sample by any suitable means.

The present collection device of the invention is thus designed for use in determining the presence or amount of an analyte in an oral sample such as saliva which is collected from a person being tested for said drug or analyte, and which will feature a collection wand having an absorbent positioned at its distal end so that the collector can absorb an oral sample from the inside of the mouth when said collector is inserted inside the mouth of the test subject. In the present invention, the collector wand is used along with a scent or odor capable of stimulating saliva production, which is generally positioned on the collector wand in such a manner that the scent or odor will be close enough to the test subject's nasal passage so as to stimulate the subject's saliva production when the collector wand is inserted inside the mouth of said test subject. In the general case, the scent or odor will be positioned so that it remains outside of the mouth during collection of the sample and does not interfere with the collection process. Among the many suitable forms of the device in accordance with the invention, some exemplary embodiments may be observed in FIGS. 1-3. In general, as observed in FIGS. 1a and 1b, the device of the present invention is comprised of a collector wand 10, which is made of any suitable durable material, such as a hard plastic, and features an absorbent material such as a sponge 18 which will be generally located at the distal end of the wand. In one preferred embodiment, the wand will be comprised of a handle 12 which has a distal handle portion 14 which is shaped so as to provide compression on the sponge so as to express the oral sample when so desired. This may involve the movement of the distal portion 14 or the movement of the distal end 25 of the handle so that the sponge is compressed against the distal portion of 14. The distal end 25 can take any suitable form, but is preferred to be in the form of a hard disk which will be used to retain the sponge 18 of the collection wand. In these cases, the distal end 25 will be connected to a stem 16 which is designed to fit inside a hollow handle 12 and will thus be movable inside the handle to cause the sponge to be compressed when so desired to express the oral sample. In a procedure wherein the oral sample is introduced into a buffer following sample collection, the sponge end of the wand is placed inside a suitable buffer container or vial and pressed downward so that the distal handle portion 14 comes down upon the distal end 25, thus compressing the sponge 18 and expressing the saliva or other sample collection from the oral swab.

In the present invention, any absorbent material which can be disposed at the distal end of the wand 10 will be suitable for use in the invention, and one skilled in the art would recognize that there are many absorbent materials which would be suited for this purpose. In the embodiment as shown, the absorbent comprises a sponge, but many other suitable materials, e.g., cotton, cellulose, PVA, and other hydrophilic polymers that expand as they wet can be used as the absorbent, and this the description that follows relating to the use of a sponge is only exemplary of the absorbents that can be utilized in the invention. As can be observed in the drawings, the sponge 18 may be in the form of small rings 17, such as observed in FIG. 1a, or may be a single larger sponge 18 having a diameter roughly equal to the distal portion 14 of the handle 12. Once again, in either case, it is desirable that the sponge be located at the distal end of the wand 10 so that it can be readily inserted in the mouth to collect the oral sample, and that following completion of the collection process, it can be compressed so that the sample is expressed when so desired into a suitable container or other appropriate portion of a testing device, e.g., applied directly onto a suitable test strip.

Figure 2:
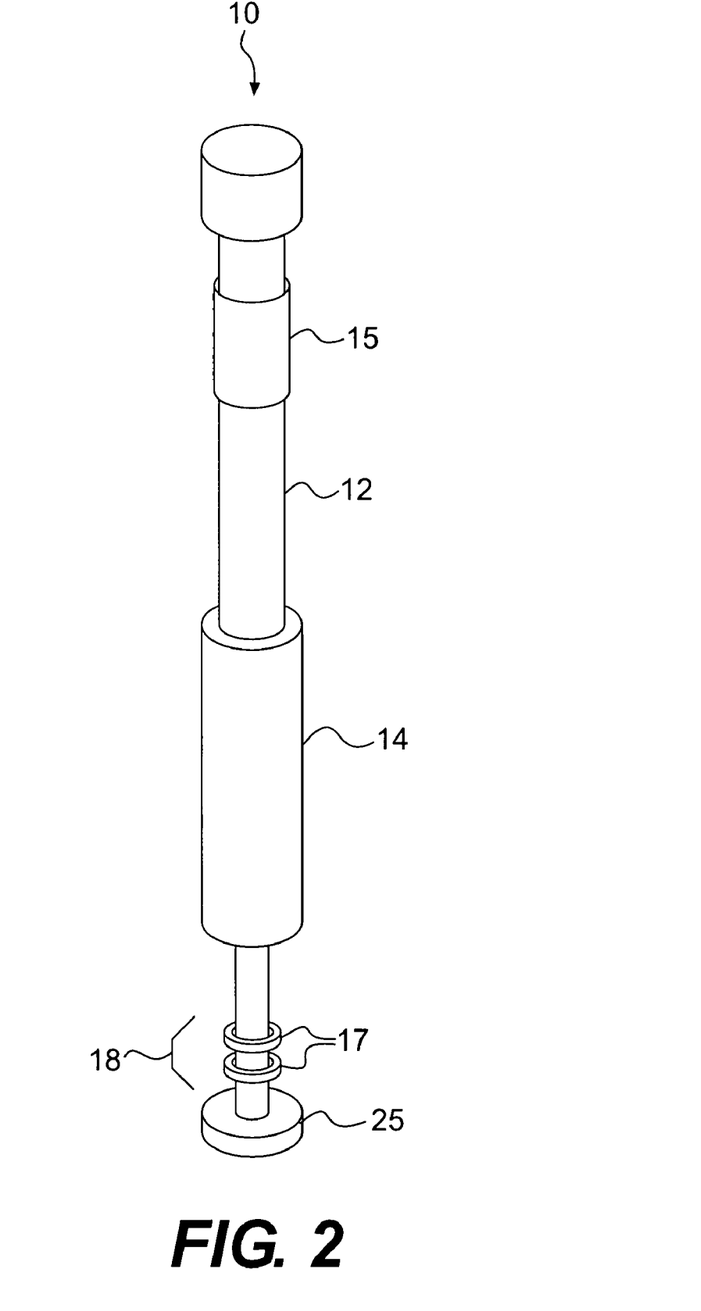
FIG. 2 is an alternative embodiment of the collection device of the present invention.

In accordance with the present invention, a scent or odor is used to enhance or stimulate the saliva production during the testing procedure, and this scent or odor will generally be located in such as a position as to be presented to the test subject's nose or nasal passage during the saliva collection step. As such, the scent or odor will generally be located towards the proximal end of wand 10. This scent or odor may be affixed in any suitable manner so that the scent or odor will reach the subject during testing, and such measures may include the scent or odor being affixed to the wand by means of an adhesive strip, being clipped to the wand in any suitable manner, or even being impregnated into the plastic wand at least in a suitable location so that it will stimulate the saliva production when the wand is used for saliva collection. For example, as shown in FIG. 2, the wand may have a scent or odor attached by means of an adhesive strip 15 which can be affixed to the wand at a location suitable to be presented to the subject's nostrils during a testing procedure. As shown in FIG. 2, this position is generally towards the proximal end of wand 10, but may be affixed in any suitable location wherein the scent or odor will be in the vicinity of the subject's nostrils so as to be inhaled and stimulate saliva production. In the device of FIG. 2, the wand 10 is shown with the adhesive strip 15 at a position generally towards the proximal end of the wand, affixed to handle 12 which is connected to enlarged distal portion 14 which will slide down stem 16 when so desired to express the sample from sponge 18 when expression of the completed sample is desired.

Figure 3:
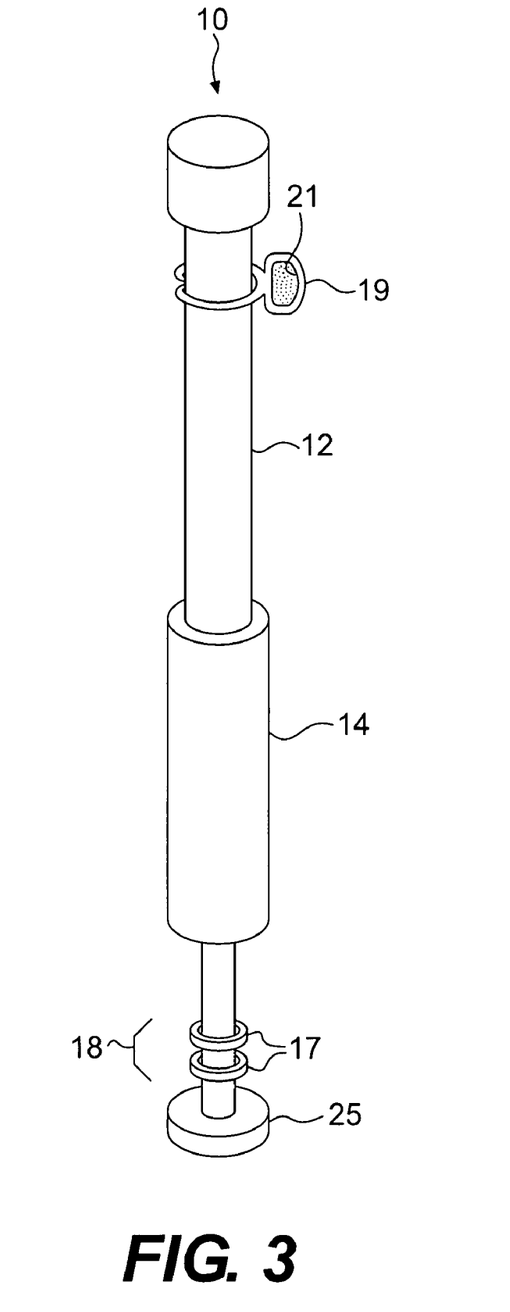
FIG. 3 is an alternative embodiment of the collection device of the present invention.

An alternative mode of the invention is shown in FIG. 3 wherein clip 19 replaces the adhesive form 15 of the previous embodiment. The clip 19 will be any suitable piece, such as made of plastic, metal, etc., which will have a portion containing a scent or odor 21, and which will be snugly attachable to wand 10, such as on handle 12. As shown, once again the location of the scent or odor clip 19 will be generally at a suitable place on the wand 10 so as to be presented to the subject's nose during a testing collection procedure and thus stimulate saliva production. In this embodiment, the clip 19 is placed at a location generally towards the proximal end of wand 10, but it may be located at any suitable location at the wand wherein it will be in the vicinity of the subject's nasal passages, and yet not interfere with the collection of saliva by the sponge region 18.

Figure 1A:
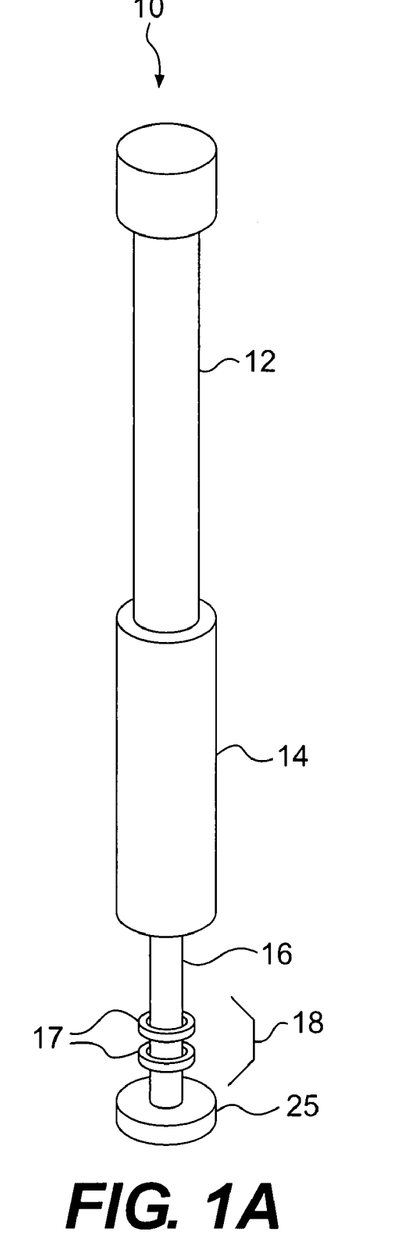
FIGS. 1a and 1b are perspective views of an embodiment of a collection device in accordance with the present invention.
Figure 1B:
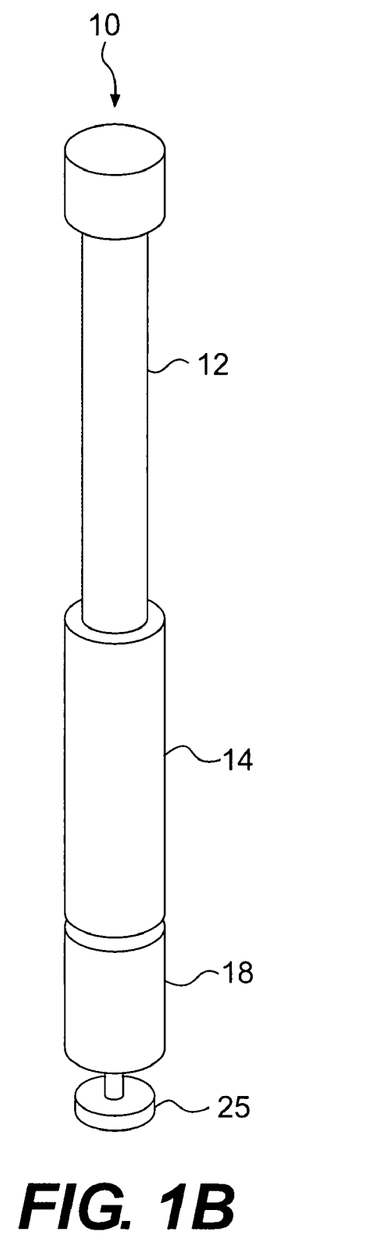

An even further embodiment of the present invention will have the scent or odor directly impregnated into the wand 10 in at least one location so that the scent or odor is presented to the subject during the sample collection procedure. In one suitable example in this regard, the scent is impregnated into the plastic handle 12 of the wand 10 during the process of making the handle, and this scent or odor will be located in a position suitable to stimulate saliva during the collection procedure. An example of such a device is shown in the apparatus of FIGS. 1*a* and 1*b*, wherein the plastic material is impregnated at a suitable location so as to give off a scent or odor, and this scent may be impregnated into one or more parts of the wand, e.g., the handle portion 12, the distal handle portion 14, stem 16, etc.

In accordance with the invention, the desired scent or odor useful in the device of the invention may be any non-toxic odor which can be readily affixed to or impregnated into the device of the present invention and which will stimulate the production of saliva in the test subject. Such scents or odors are readily available, and may constitute natural materials or artificial scents which are commonly manufactured for a variety of products. Typically, the scents or odors of the invention will be of a food product which generally stimulates salivation, and these scents and odors include any such scent or odor naturally or artificially added to a food product or other product for oral use (e.g., mouthwashes, toothpastes, etc.) Accordingly, there will be a wide variety of suitable scents or odors as would be recognized by one skilled in the art, including, for example, scents of mint, menthol, wintergreen, melon, orange, lemon, lime, apple, cherry, pineapple, strawberry, almonds, peanuts, chocolate, pizza, etc. As indicated above, one skilled in the art would readily be able to provide these scents whether naturally or artificially created.

Figure 4:
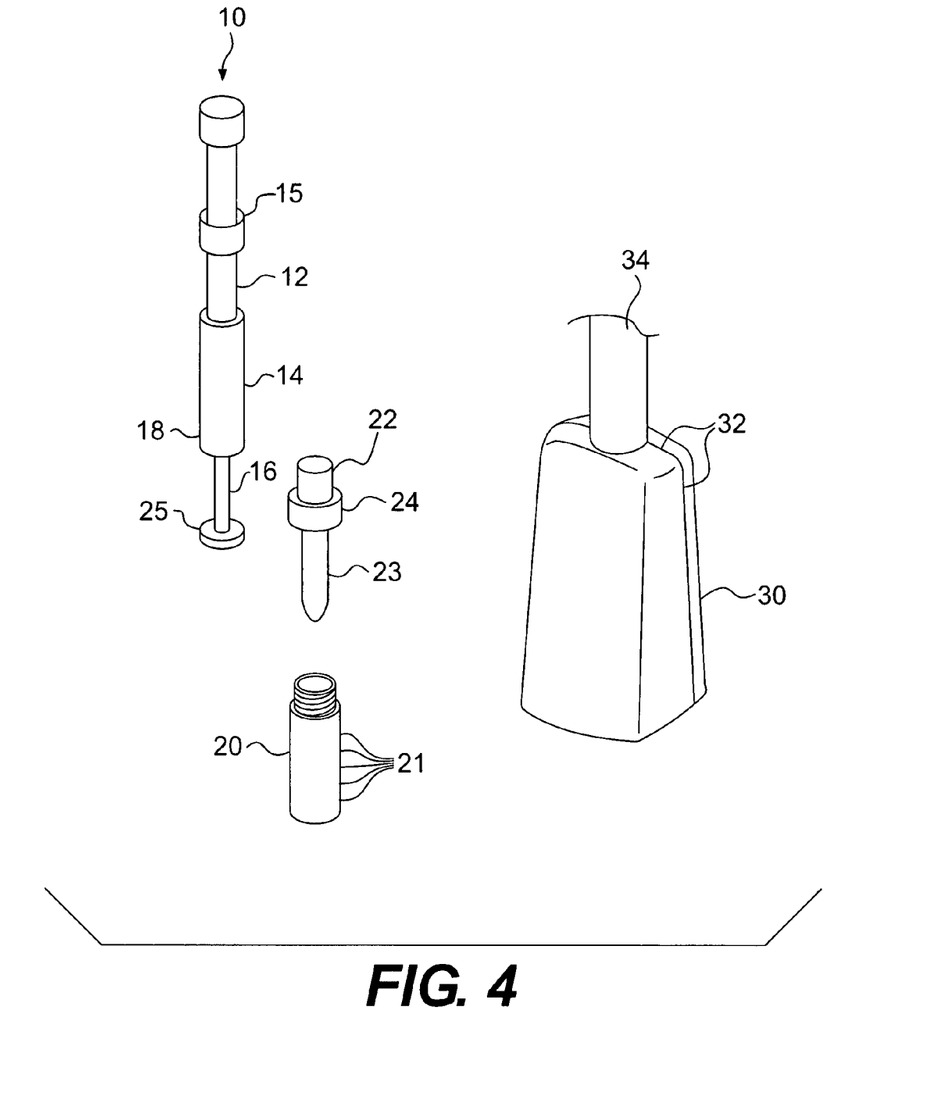
FIG. 4 is an overview of a testing system in accordance with the present invention including the collection device of the present invention prior to obtaining the oral sample, a buffer vial for receiving the oral sample, a pipette or dropper which can transfer the sample mixture into reaction wells, and a testing device containing the reaction wells and test strips for conducting the immunoassays to allow the qualitative or quantitative testing of drugs of abuse.

An example of the system utilizing the device 10 of the present invention is shown generally in FIG. 4. As will be described further below, the extraction wand 10 of the present invention is shown in the drawing of FIG. 4 which generally shows the parts of the extraction system of the present invention. This wand generally comprises a handle 12 having a hollow internal cavity having at least one latching means internally positioned for retaining a stem 16 constructed to fit slidably into the cavity so that the handle can slide downward over the stem and ultimately cause the sponge 18 to express the body fluid sample obtained from a patient. The handle will preferably have a generally cylindrical shape and will be configured so that the distal end 14 of the handle 12 will be able to apply compression to a sponge 18 positioned on the stem which will be used in the collection of a body fluid sample from the individual to be tested. Both the handle and stem may be made of a suitable sturdy sterilizable material such as hard plastic.

At the bottom end of stem 16, at the portion where the stem will be outside of the handle, there will be located a suitable sponge 18 capable of absorbing body fluids from the subject being tested. In the preferred embodiment, the sponge will be in the form of a compact disk which will be positioned on the distal end of the stem so that it is exposed and may be utilized to collect a sample from an individual who is being tested for the presence of drugs of abuse or other analytes. The sponge is preferably an untreated medical grade absorbent fiber sponge which will expand during the collection process, and if desired, more than one sponge may be used with the wand of the device.

As described herein, a system for analyte testing in accordance with the invention is also provided which includes means for buffering the oral sample before being introduced into the testing device, and in the preferred embodiment, this buffering means includes a buffer solution which is retained in a buffer vial designed to receive the expressed sample from the sponge of the collector wand after the handle is brought downward and the sample is expressed from the sponge. This buffer vial or container 20 is depicted in FIG. 4, and this vial may include gradations 21 so as to indicate the total volume of solution and to allow the testing of the present invention to be performed quantitatively or semi-quantitatively (i.e., those testing procedures which involve some aspects of quantitative testing and some which involve qualitative testing) in addition to qualitatively. The ability to use the graduated vial (and dropper or pipette as described below) for such quantitative or semi-quantitative testing so as to quantify when so desired the concentration of an analyte being detected by the testing device will be well understood by one skilled in the art. For example, the present invention will thus allow quantification in terms of weight and volume, i.e., measurements in terms of weight/weight or volume/volume will be made possible. The container vial 20 will have a matching dropper 24 having a bulb 22 and preferably a volumetric line 23 which can be used to remove measured amounts of the solution containing the oral sample of the invention.

The extraction system of the present invention thus includes means such as vial 20 which is designed to receive the sample from the collection sponge and which preferably includes a buffer material which is designed to improve the sensitivity of the testing procedure such as by removing interfering particles from the sample solution and/or reducing the viscosity of the solution. As indicated above, the buffer solution is preferably one that is formulated to solubilize the analytes of interest, thereby making them available to react with the labeled antibodies in an immunoassay. In addition, the buffer is designed to remove or denature interferants so as to improve the ability of the sample material to be detected in a lateral flow immunoassay, and in the example when the oral sample is saliva, the buffer solution can promote the breakdown of mucins in the saliva sample and thus enhance the sensitivity of the immunoassay based on this saliva sample. In general, the buffer solution will thus include those reagents which are capable of breaking down the interferants in a sample, e.g., mucins in saliva, so that these interferants do not restrict the capillary flow of the sample through the test strip, in order to have a rapid test of target compounds in a more accurate manner than heretofore possible. The buffer will thus be utilized in pre-treatment steps as appropriate for the sample being tested and will generally include specific reagents which can solubilize the analyte, dilute or denature interferants, modify analyte structure, and/or release analyte from binders.

Accordingly, the extraction buffer will generally be any suitable solution which serves to break down, sanitize or remove interferants so as to reduce the viscosity of the oral sample, e.g., saliva, and ensure efficient capillary flow on the test strips, and such buffers are readily known in the art.

As indicated above, in order to carry out a testing procedure in accordance with the present invention, the collector wand 10 is swabbed in the subject's mouth for the desired oral sample, e.g., saliva, buccal cavity fluid, buccal cells, etc., so that the sponge 18 at the distal end of the wand will absorb the sample from the subject. In the preferred system, the wand 10 will have a scent or odor associated with it and located at a location on the wand that will generally face the test subject at the time the test is being conducted so that the scent or odor will stimulate the production of saliva and thus increase the efficiency of the test by increasing the amount of the oral sample that can be collected during the testing procedure. In an exemplary process, the collector wand 10 of the invention may be used to test a saliva sample, and this process will be described in more detail below, although one skilled in the art would recognize that the steps used in the collection process would vary as needed for other oral samples. In the preferred saliva collection process, the wand 10 has been prepared for saliva stimulation by means of either an attachment having the desired scent or odor, or by making the wand out of a plastic material into which a desired odor may be impregnated. In one example of this feature, the scent or odor may be attached to the collector wand 10 by means of an adhesive strip 15 which contains the desired scent or odor. In this embodiment, when the sponge 18 at the distal end of collection wand 10 is placed between the cheek and gum of the donor subject for a suitable period of time, e.g., at least one minute, the scent or odor adhesive 15 will be located on the wand in such a manner that the scent or odor will generally be in the vicinity of the nostrils of the test subject, and the inhalation of the scent or odor by the test subject will stimulate saliva production and maximize the amount of the sample that will be collected by the device 10.

Figure 5:
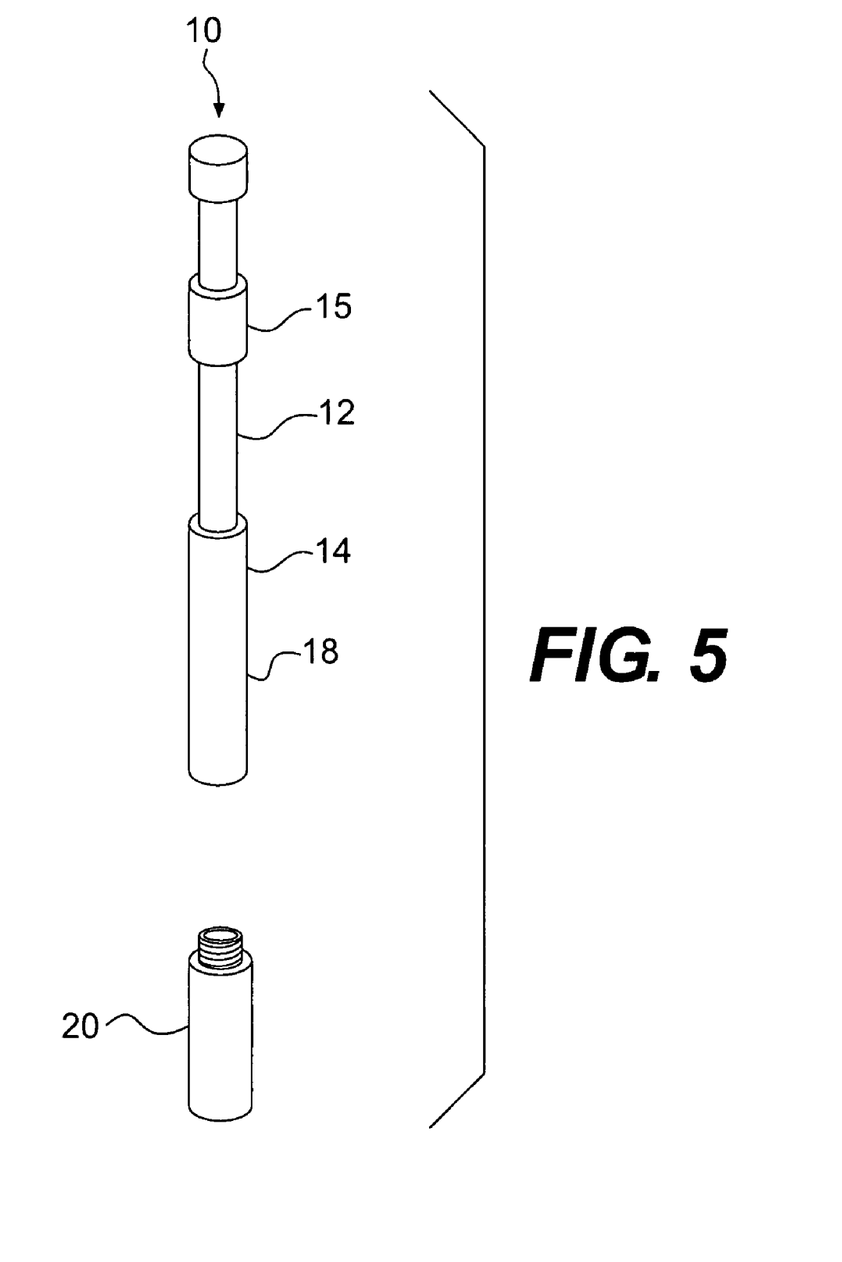
FIG. 5 is a front view of the collector wand of the invention and a buffer vial following collection of the oral samples wherein the sponge at the distal end of the wand has expanded due to absorption of the sample body fluid.
Figure 6:
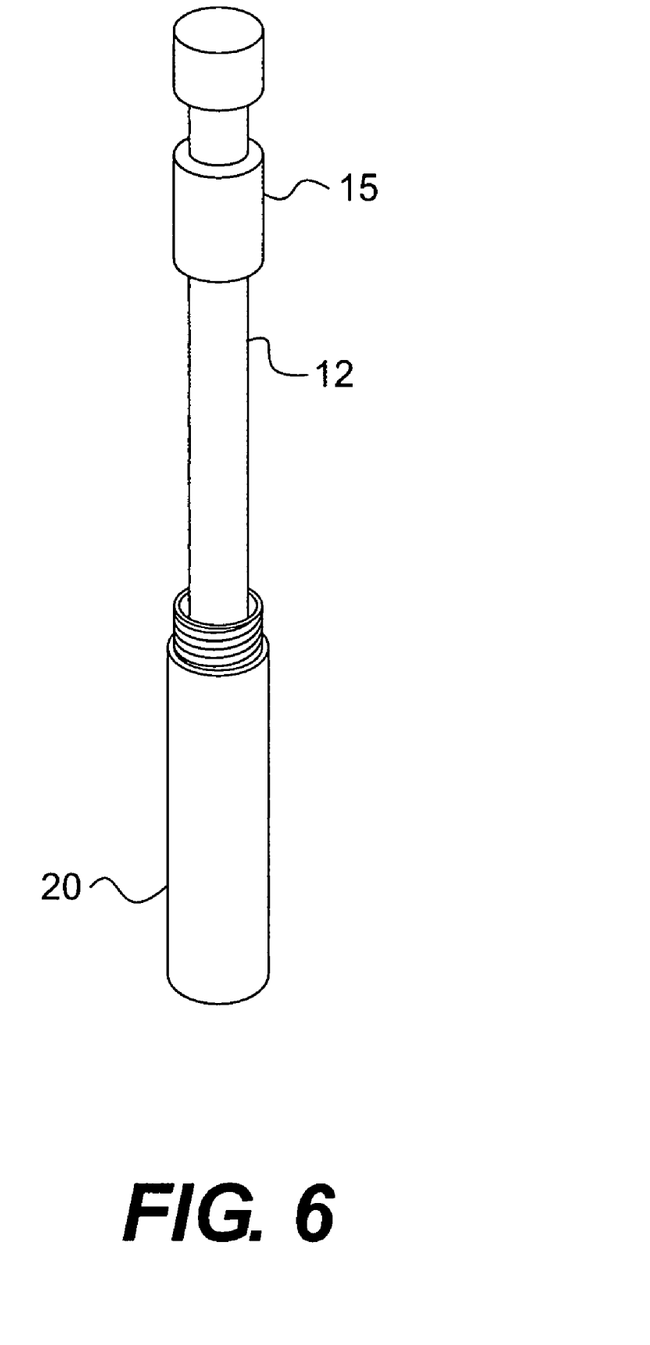
FIG. 6 is a front view of the collector wand of the invention inserted into the buffer vial so that the oral sample may be expressed from the sponge and mixed with the buffer solution in the vial.

During the testing procedure, the sponge 18 should expand which reflects the absorption of a suitable oral sample such as saliva, and in any event the procedure should continue until the sponge at the distal end of the stem is fully expanded, indicating that a suitable amount of saliva has been absorbed from the subject. In one suitable analyte testing procedure in accordance with the invention, the collected saliva from sponge 18 may be expressed into a vial 20 containing a suitable buffer to assist with the expression and solubilization of the saliva sample. This configuration is shown in FIG. 5 wherein the sponge 18 following collection of the sample of saliva from the subject has expanded and is ready for expression into buffer vial 20. In this example, at this point the collector wand 10 with its expanded sponge 18 which has been removed from the subject, is placed into the buffer vial 20 so that the sample may be fully expressed from the sponge and enter into the buffer solution contained in the buffer vial, and the placement of the sponge or distal end of wand 10 into buffer vial 20 is shown in FIG. 6. At this point, buffer solution from the vial 20 will initially be absorbed into the sponge 18, and as indicated above, the sample and buffer may be expressed from the collector wand by bringing the handle down towards the sponge so that the distal end of the handle compresses the sponge, and the handle will be brought into locking position when the latching means in the internal cavity of the handle is brought into contact with the outermost protrusion in the stem. In one mode of the invention, expression of saliva may be maximized by a locking mechanism which can maintain the wand in such a position as to expel a maximum amount of the oral sample into the buffer vial 20, and such a locking mechanism is described in detail in U.S. application Ser. No. 11/621,261. In this system, locking the handle in position will ensure that compression of the handle over the sponge is maintained and the expression of the saliva sample into the buffer solution is maximized.

Accordingly, as indicated above, in the preferred operation of the present invention, a wand having a scent or odor attached or impregnated as described above is used to recover an oral sample for analyte testing, and this wand contains a sponge at its distal end which is used to collect the oral sample for further processing in an analyte testing system. For example, the obtained oral sample may be placed inside a buffer vial containing a buffer solution which will assist in the removal or reduction of interferants in the oral sample, e.g., mucins when the sample is saliva. After the expression of the oral sample into the container or vial 20, the sample is ultimately made ready to be tested in a high sensitivity immunoassay, such as those involving test strips containing immunological binding agents, as will be detailed below.

One suitable testing device 30 for use with the collector wand of the present invention, is shown in FIG. 4, and such a device is designed to be used with immunoassay test strips which may be held outside the reaction well until it is time to conduct the immunoassay test, such as using means for holding 34 as shown in FIG. 4. This holding means if preferably slidable so that the strips may be brought down into communication with the reaction wells after a suitable incubation time has elapsed. The device 30 also preferably contains reaction wells 32 for the introduction of the buffer solution containing the oral sample as obtained above, and the test can be completed by having the immunoassay strips housed in holding means 34 brought downward after the buffer solution with the oral sample is placed in reaction wells 32. As will be well understood by one of ordinary skill in the art, the immunoassay system may involve a suitable immunological identifying reagent such as a gold particle attached to a suitable antibody or antigen which can be used to target a particular drug of abuse or other analyte, and these materials are utilized in conjunction with a test strip wherein the test fluid moves through the strip via capillary action, and the presence of a desired analyte is determined by the presence of the identifying reagent at a suitable location down the test strip. In general, the identifying reagent will include a detectable component, e.g., a magnetic particles, latex, colloidal silver, colloidal gold, charcoal, a fluorescent label, etc., and this identifying reagent will be bound to a material that can bind the target analyte, e.g., an antibody, an antigen, a protein, a peptide, or any other suitable carrier molecule that can bind to the target analyte. As indicated herein, this identifying reagent may thus comprise a colloidal gold particle bound to an antibody, but many suitable identifying reagents and target-binding materials well known for this purpose may be utilized in accordance with the invention.

Figure 7:
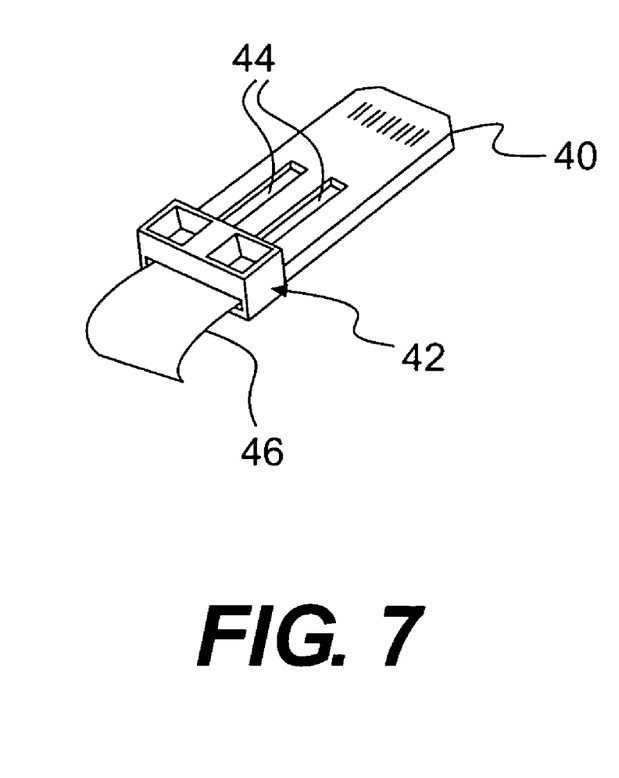
FIG. 7 is a perspective view of an alternate embodiment of the testing device used in conjunction with the collector wand of the present invention.
Figure 8A:
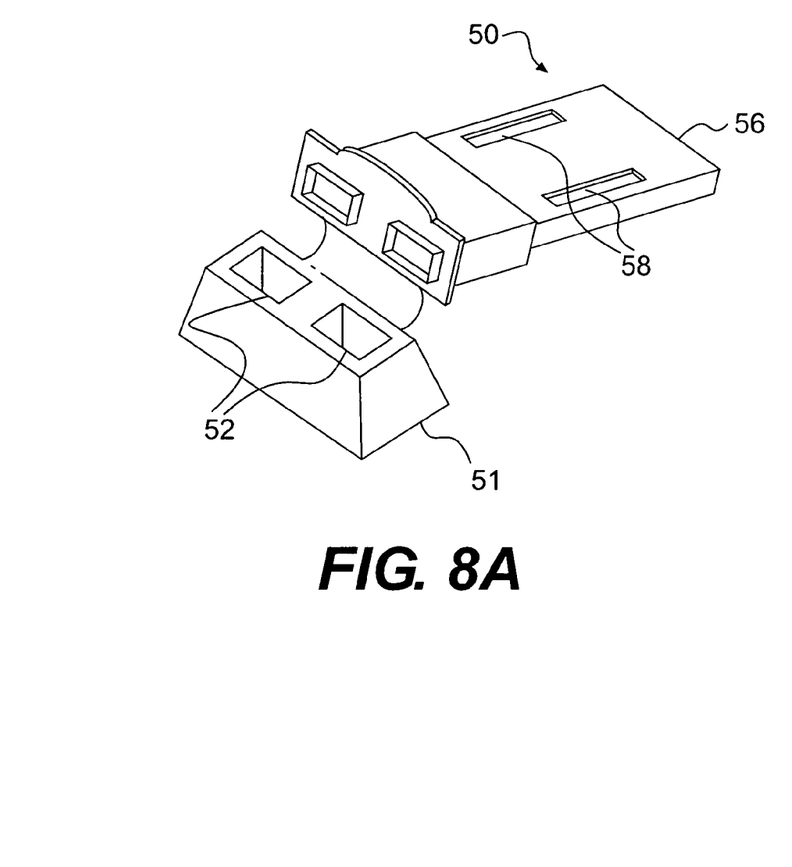
FIG. 8a is a perspective view of an alternate embodiment of the testing device used in conjunction with the collector wand of the present invention.
Figure 8B:
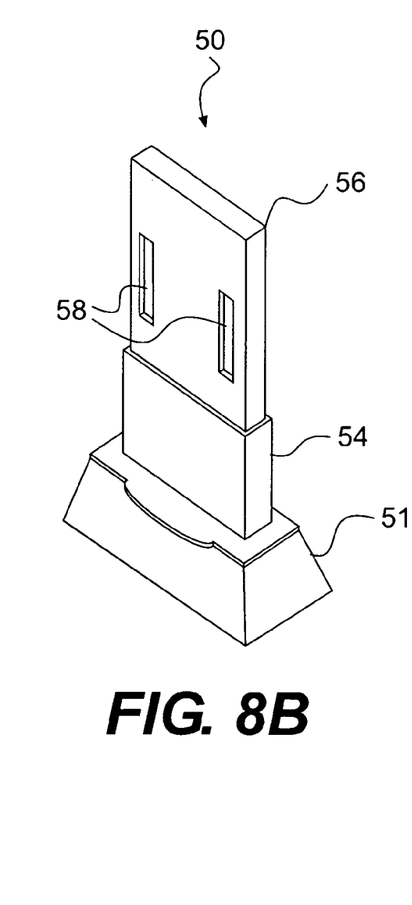

Other suitable testing systems in accordance with the scented collector wand of the present invention are shown in FIGS. 7, 8a and 8b. In one alternative of the testing system useful with the scented wand of the invention, the immunoassay test strip may be separated from the reaction well using a suitable membrane or other barrier which is removed or which dissolves after a given amount of time so as to allow the sample solution to be introduced to the immunoassay test strip. Alternative test devices incorporating such a barrier are shown in FIGS. 7, 8a and 8b. In FIG. 7, this alternative test device 40 is shown with modified reaction wells 42 which are placed over a housing which includes test strips 44. In this configuration, the buffer solution containing the body fluid sample which is obtained as outlined above is poured directly into the reaction wells which contain the gold-labelled antibody or other suitable binder or identifying reagent. The buffer and sample are allowed suitable time to mix with the antibody, and after a suitable incubation period has elapsed, and removable barrier strip 46 is provided between the bottom of the reaction well and the immunoassay test strip which is removed so that the labeled sample solution can now contact the immunoassay test strip and begin the lateral flow immunoassay test.

In a further alternative embodiment, such as shown in FIGS. 8a and 8b, the reaction wells 42 may be made sealable by providing caps 48 which fit tightly over the reaction wells and seal them after the solution has been placed in the wells. In this embodiment, the sealing of the reaction wells allows for the sample as obtained from the scented collector wand of the invention and buffer solution to be further mixed with the colloidal gold by shaking or otherwise imparting energy to the wells, and this will once again facilitate mixing of the solution and the breaking down of the interferants, e.g., mucins in saliva, so as to increase the sensitivity of the testing procedure. Once again, in this embodiment, a removable barrier such as strip 46 is provided which is removed in order to start the lateral flow immunoassay to proceed. This strip may be pulled out when desired to start the testing process following a suitable period of incubation, and it is further possible that the barrier might be constructed of a dissolvable material which is only designed to breakdown after the given incubation period has elapsed.

Drugs targeted by the test procedure can be any suitable drug or other compound of interest which may be detectable in an oral fluid, e.g., amphetamines, benzodiazepines, cocaine, methadone, methamphetamines, opiates, phencyclidine (PCP) and THC (in either its parent form of metabolite form).

Test strips suitable for use in the invention include those described, e.g., in U.S. Pat. App. Pub. 2001/0012637, said application incorporated herein by reference. In general, these test strips may be of the type made by companies such as Inverness Medical of Switzerland, Pharmatech of San Diego, Calif. and Arista Biological of Bethlehem, Pa., along with a number of other manufacturers. Such test strips are characterized as immunoassay strips and employ an identifying reagent based on colloidal gold chemistry or other identification systems such as described above. These test strips are configured so as to conduct a lateral flow immunoassay when one end is brought into contact with the test solution, and the results of the test are read in a test area preferably coinciding with a visual opening in the test device. As indicated above, these test strips can indicate the presence or absence of drugs of abuse including amphetamines, benzodiazepines, cocaine, methadone, methamphetamines, opiates, phencyclidine, PCP and THC, or other analytes when so desired.

Still other testing devices and systems compatible for use with the collector wand and methods of the present invention include those devices as described in detail in other US patent applications including U.S. Ser. No. 11/443,050, filed May 31, 2006, U.S. Ser. No. 11/252,599, filed Oct. 19, 2005, and U.S. Ser. No. 11/167,227 filed Jun. 28, 2005, all of said applications incorporated herein by reference.

In summary, in the present invention, a general device and process for collecting oral samples such as saliva is provided wherein a latchable collector wand having an absorbent sponge at its distal end can absorb a sample by insertion into the mouth of the person to be tested, and sponge is swabbed until it becomes fully saturated. The wand contains a scent or odor so as to stimulate the production of saliva when the collection procedure is taking place. The collector wand is then removed and the oral sample is extracted from the sponge end into a suitable container or vial which preferably contains a buffer agent or other reagent which can begin the process of breaking down the interferants in the sample such as mucins when the oral sample being tested is saliva. As set forth above, when the sponge end of the wand is placed in the buffer solution so that the buffer solution becomes absorbed in the sponge, the handle of the collector wand of the invention is brought down over a stem so that it will compress the sponge so that a maximum amount of the sample is expressed from the sponge and into the buffer solution. This buffer container or vial is preferably sealed such as with a removable cap, and the resulting buffer solution may be dispensed using a dropper or pipette into a reaction well of the test device which includes a suitable identifying reagent and target-binding material to be used in conjunction with an immunoassay test strip. This identifying reagent may be a complex such as a gold-labeled antibody wherein the colloidal gold is bound to an antibody that can bind to the target analyte, and may be in the form of a dry dot, dry powder, tablets, lyophilized materials, a pellet, or other suitable form.

To complete the process, after a period of incubation of the sample solution with the identifying reagent, an immunoassay test strip which is designed to test for particular drugs of abuse or other analytes via a lateral flow immunoassay, and which is configured in conjunction with the labelled antibody so as to evidence the presence or absence of the target drug or analyte in the sample, is introduced into the reaction well to allow the lateral flow immunoassay to take place. The immunoassay may be carried out by either dropping the test strip into the reaction well by means of a slidable test strip holder, or by other means such as by the removal of a barrier between the reaction well and the test strip which allows the sample solution to come into contact with the test strip and start the immunoassay. In the preferred process, in addition to a visible means for determining the presence or absence of the drug or analyte being tested, the test strips will contain means to evidence that the test has been successfully conducted, i.e., the lateral flow process has been completed, so that the person reading the test results will know that the test is a valid one. The test result is preferably viewed at a specific portion of the strip, such as that portion which coincides with an opening in the testing device housing.

Thus it can be seen that the present invention discloses an oral sample testing device which maximizes the production of saliva in the test subject by presenting to that subject a scent or odor capable of stimulating saliva production during the step wherein the oral sample is collected. The present device thus allows for testing of drugs of abuse or other analytes from such samples with very high sensitivity and with minimal unreadable tests due to low saliva production, e.g., dry mouth.

It will be understood that the description of the embodiments provided herein are merely exemplary of the invention, and thus there other embodiments and modifications not described above which are contemplated as part of the present invention and which thus are considered to be within the scope of the invention.

What is claimed is:

1. An absorbent collection device for use in testing an analyte from an oral sample collected from a person being tested for an analyte comprising:
    a collector wand having an absorbent positioned so that the collector can absorb an oral sample from the inside of the mouth when said collector is inserted inside the mouth of the test subject;
    a scent or odor capable of stimulating saliva production disposed on said collector in such a manner that the subject's saliva production is stimulated when said collector is inserted inside the mouth of said test subject;
    wherein the scent or odor is positioned so that it remains outside of the mouth during collection of the sample and does not interfere with the collection process, and remains generally in front of the test subject's nasal passage during an oral sample collection procedure.

2. The absorbent collection device according to claim 1 further comprising means for expressing the oral sample from said absorbent so that said sample may be subject to a test for said analyte.

3. The absorbent collection device according to claim 1 wherein the scent or odor is contained in an adhesive wrapped around said collector wand.

4. The absorbent collection device according to claim 1 wherein the scent or odor is contained in a separate piece attached to said collector wand.

5. The absorbent collection device according to claim 1 wherein the scent or odor is impregnated into said collector wand.

6. The absorbent collection device according to claim 1 wherein the absorbent comprises a material selected from the group consisting of a sponge, cotton, cellulose, polyvinyl acetate (PVA), and any other hydrophilic polymers that expand as they wet.

7. The absorbent collection device according to claim 1 wherein the collector wand is constructed of a durable hard plastic material.

8. An immunoassay test device for testing of an analyte from an oral sample comprising the collection device according to claim 1, means for receiving the oral sample, means for adding an identifying reagent to the oral sample, and immunoassay means for determining the presence of an analyte in the oral sample.

9. The immunoassay test device according to claim 8 wherein the immunoassay means is a test strip containing the identifying reagent and wherein the test is conducted by introducing the oral sample onto the test strip.

10. The immunoassay test device according to claim 9 wherein the identifying reagent comprises a material selected from the group consisting of magnetic particles, latex, colloidal silver, colloidal gold, charcoal, and a fluorescent label.

11. The immunoassay test device according to claim 10 wherein the identifying reagent is bound to a material that can bind the target analyte selected from the group consisting of an antibody, an antigen, a protein, a peptide, and any carrier molecule that can bind to the target analyte.

12. The immunoassay device according to claim 8 further comprising a buffer solution into which the oral sample is expressed following collection of the oral sample.

13. A method for stimulating the production of saliva during an oral sample collection procedure comprising:

(a) providing an absorbent collection device according to claim 1; and (b) inserting said collection device in the mouth of a test subject so that the scent or odor on the collector wand will stimulate saliva production at the time of testing.

14. The method according to claim 13 wherein the scent or odor is affixed to the collector wand of the collection device by means of an adhesive.

15. The method according to claim 13 wherein the scent or odor is located on a separate part which is affixed to the collector wand.

16. The method according to claim 13 wherein the scent or odor is located on a separate piece which is affixed to the collector wand.

17. The method according to claim 13 wherein the oral sample collected is selected from the group consisting of saliva, buccal cavity fluid, and buccal cells.

18. A method for conducting an immunoassay for an analyte in an oral sample comprising:

(a) providing an absorbent collection device according to claim 1;

(b) inserting said collection device in the mouth of a test subject so that the scent or odor on the collector wand will stimulate saliva production at the time of testing;

(c) collecting the oral sample in the absorbent of the collector wand;

(d) expressing the collected oral sample and introducing said oral sample into an immunoassay test device having an identifying reagent that can determine the presence of an analyte in said oral sample.

19. The method according to claim 18 wherein the oral sample collected is selected from the group consisting of saliva, buccal cavity fluid, and buccal cells.

20. The method according to claim 18 wherein the identifying reagent comprises a material selected from the group consisting of magnetic particles, latex, colloidal silver, colloidal gold, charcoal, and a fluorescent label.

21. The method according to claim 18 wherein the identifying reagent is bound to a material that can bind the target analyte selected from the group consisting of an antibody, an antigen, a protein, a peptide, and any carrier molecule that can bind to the target analyte.

* * * * *